US008487102B2

(12) United States Patent
Jablonski et al.

(10) Patent No.: US 8,487,102 B2
(45) Date of Patent: Jul. 16, 2013

(54) PYRRAZOLOPYRIDINE COMPOUNDS AS DUAL NK1/NK3 RECEPTOR ANTAGONISTS

(75) Inventors: Philippe Jablonski, Steinbrunn-le-Haut (FR); Matthias Nettekoven, Grenzach-Wyhlen (DE); Angelique Patiny-Adam, Rosenau (FR); Hasane Ratni, Habsheim (FR); Heinz Stadler, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 301 days.

(21) Appl. No.: 13/083,636

(22) Filed: Apr. 11, 2011

(65) Prior Publication Data

US 2011/0257402 A1   Oct. 20, 2011

(30) Foreign Application Priority Data

Apr. 20, 2010   (EP) .................... 10160481

(51) Int. Cl.
C07D 471/04   (2006.01)
(52) U.S. Cl.
USPC ........................................ 546/119
(58) Field of Classification Search
USPC ........................................ 546/119
See application file for complete search history.

(56) References Cited

U.S. PATENT DOCUMENTS 5,972,938 A   10/1999   Rupniak et al.

FOREIGN PATENT DOCUMENTS

| EP | 1192952 | 4/2002 |
| WO | WO95/16679 | 6/1995 |
| WO | 95/18124 | 7/1995 |
| WO | WO95/23798 | 9/1995 |
| WO | 03068773 | * 8/2003 |
| WO | WO2005/002577 | 1/2005 |
| WO | WO2006/013050 | 2/2006 |

OTHER PUBLICATIONS

Hoffmann-Emery et al., J. Org. Chem. 71:2000-2008 ( 2006).
Neurosci. Res. 7:187-214 ( 1996).
Psychiatric Disorders Study 4, Schizophrenia (Decision Resources, Inc.) (Jun. 2003).
Plattner et al., "Current Opinion in Investigational Drugs" 2(7):950-956 ( 2001).
Longmore et al., "Canadian Journal of Physiology & Pharmacology" 75:612-621 ( 1997).
"PCT International Search Report PCT/EP2011/055971 dated Apr. 15, 2011".
Maggi et al., "Autonomic & Autacoid Pharmacology" 13:23-93 ( 1993).
Giardina et al., "Exp. Opinion on Therapeutic Patents" 10(6):939-960 ( 2000).
Navari et al., "The New England Journal of Medicine" 340(13):190-195 ( 1999).
Kramer et al., "Science" 281:1640-1645 ( 1998).

* cited by examiner

Primary Examiner — Niloofar Rahmani

(57) ABSTRACT

The present invention relates to a compound of formula I

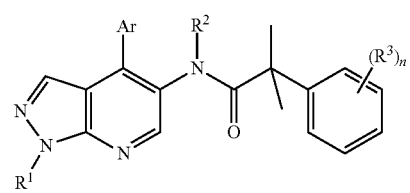

wherein $R^1$, $R^2$, $R^3$, Ar, and n are as defined herein or to a pharmaceutically active acid addition salt. Compounds of formula I show a high affinity simultaneously to both the NK1 and the NK3 receptors (dual NK1/NK3 receptor antagonists), useful in the treatment of schizophrenia.

9 Claims, No Drawings

PYRRAZOLOPYRIDINE COMPOUNDS AS DUAL NK1/NK3 RECEPTOR ANTAGONISTS

PRIORITY TO RELATED APPLICATION(S)

This application claims the benefit of European Patent Application No. 10160481.7, filed Apr. 20, 2010, which is hereby incorporated by reference in its entirety.

BACKGROUND OF THE INVENTION

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956 and *Psychiatric Disorders Study* 4, *Schizophrenia*, June 2003, Decision Recources, Inc., Waltham, Mass.).

In addition, EP 1 192 952 describes a pharmaceutical composition containing a combination of a NK3 receptor antagonist and a CNS penetrant NK1 receptor antagonist for the treatment of depression and anxiety.

Now it has been found that the combination of the antidepressant, mood enhancing properties of NK1 receptor antagonism and the antipsychotic effects of NK3 receptor antagonism are suitable to treat both positive and negative symptoms in schizophrenia.

This advantage may be realized in the administration of an ideal drug against schizophrenia.

NK1 receptor antagonists may be useful for the treatment of diseases, such as inflammatory conditions including migraine, rheumatoid arthritis, asthma, and inflammatory bowel disease as well as mediation of the emetic reflex and the modulation of central nervous system (CNS) disorders such as Parkinson's disease, anxiety, pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

The neurokinin-1 receptor antagonists are further useful for the treatment of motion sickness, for treatment induced vomiting or for the treatment of psychoimmunologic or psychosomatic disorders, see *Neurosci. Res.*, 1996, 7, 187-214, *Can. J. Phys.*, 1997, 75, 612-621, *Science*, 1998, 281, 1640-1645, *Auton. Pharmacol.*, 13, 23-93, 1993, WO 95/16679, WO 95/18124 and WO 95/23798, *The New England Journal of Medicine*, Vol. 340, No. 3 190-195, 1999, U.S. Pat. No. 5,972,938.

SUMMARY OF THE INVENTION

The present invention provides novel compounds of formula I and pharmaceutically acceptable salts thereof as well as pharmaceutical compositions containing such compounds. The invention also provides methods of the preparation of such compounds and compositions. The invention further provides methods for the treatment CNS disorders as discussed above, in particular the treatment of positive and negative symptoms in schizophrenia.

The present invention provides a compound of formula I

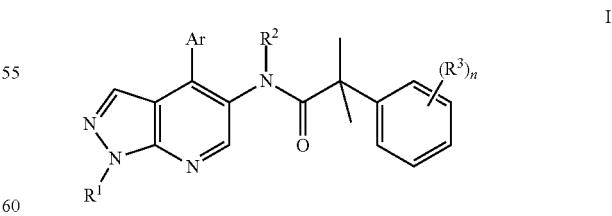

wherein
$R^1$ is hydrogen, lower alkyl, lower alkyl substituted by halogen, benzyl, —C(O)-lower alkyl, —C(O)—CH$_2$-lower alkoxy, —C(O)—C$_{3-6}$-cycloalkyl, —(CH$_2$)$_o$—C(O)—NRR', —(CH$_2$)$_o$S(O)$_2$— lower alkyl or —S(O)$_2$—NR,R';
o is 0 or 1;

R and R' are each independently hydrogen or lower alkyl, or together with the N atom to which they are attached form a 5 or 6 membered heterocycloalkyl ring;

$R^2$ is hydrogen or lower alkyl;

$R^3$ is halogen, lower alkoxy, lower alkyl substituted by halogen or lower alkoxy substituted by halogen; and when n is 2, each $R^3$ is the same or different;

n is 1 or 2; and

Ar is phenyl optionally substituted by one or two substituents selected from lower alkyl, halogen, lower alkoxy, lower alkyl substituted by hydroxy or cyano, or is a five or six membered heteroaryl group, selected from thiophenyl or pyridinyl which are optionally substituted by lower alkyl or halogen;

or a pharmaceutically active acid addition salt thereof.

The compounds of formula I can contain some asymmetric carbon atoms. Accordingly, the present invention includes all stereoisomeric forms of the compounds of formula I, including each of the individual enantiomers and mixtures thereof.

The compounds of formula I and their salts are characterized by valuable therapeutic properties. Compounds of formula I show a high affinity simultaneously to both the NK1 and the NK3 receptors (dual NK1/NK3 receptor antagonists), useful in the treatment of schizophrenia.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like.

The term "lower alkoxy" denotes the group —OR' wherein R' is a lower alkyl group as defined above.

The term "halogen" denotes chlorine, iodine, fluorine and bromine.

The term "lower alkyl substituted by halogen" denotes a lower alkyl group as defined hereinabove which is substituted by one or more, preferably one, two or three halogen atom(s), i.e. chlorine, iodine, fluorine or bromine. Particularly $CF_3$.

The term "lower alkoxy substituted by halogen" denotes a lower alkoxy group as defined above in which one or more hydrogen atom is replaced with a halogen atom.

The term "cycloalkyl" denotes a saturated carbocyclic group containing 3-6 carbon atoms.

The term "5 or 6 membered heterocycloalkyl ring" denotes a heterocyclic ring having 5 or 6 ring members comprising at least two carbon atoms as ring members and 1, 2 or 3 additional heteroatom(s) ring members selected from N, O and S, the remaining ring members being carbon atoms. Examples of 5 or 6 heterocycloalkyl rings include, for example pyrrolidin-1-yl, piperidin-1-yl, morpholinyl and the like.

The term "5 or 6 membered heteroaryl group" denotes an aromatic group having 5 to 6 ring atoms and containing one or more heteroatoms selected from nitrogen, oxygen and sulphur. Examples of 5 or 6 membered heteroaryl groups include, for example thiophenyl, furanyl, pyrrolyl, pyridinyl and the like.

The term "thiophenyl" as used herein is synonymous with "thienyl" and denotes a thiophene substituent, i.e., $C_4H_4S$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

One embodiment of the invention provides compounds of formula I, wherein Ar is optionally substituted phenyl and $(R^3)_n$ is 3,5-di-$CF_3$, for example the following compounds 2-(3,5-bis-trifluoromethyl-phenyl)-N-(1-ethyl-4-o-tolyl-1H-pyrazolo[3,4-b]pyridin-5-yl)-N-methyl-isobutyramide;

2-(3,5-bis-trifluoromethyl-phenyl)-N-[1-ethyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(2-chloro-phenyl)-1-ethyl-1H-pyrazolo[3,4-b]pyridin-5-yl]-N-methyl-isobutyramide;

2-(3,5-bis-trifluoromethyl-phenyl)-N-[4-(3,4-dichloro-phenyl)-1-ethyl-1H-pyrazolo[3,4]pyridin-5-yl]-N-methyl-isobutyramide;

2-(3,5-bis-trifluoromethyl-phenyl)-N-[1-(2,2-difluoro-ethyl)-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methyl-1H-pyrazolo[3,4-b]pyridin-5-yl]-N-methyl-isobutyramide;

N-[1-benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;

2-(3,5-bis-trifluoromethyl-phenyl)-N-[1-ethyl-4-(4-fluoro-2-methoxy-phenyl)-1H-pyrazolo[3,4-b]pyridin-5-yl]-N-methyl-isobutyramide;

2-(3,5-bis-trifluoromethyl-phenyl)-N-[4-(2-chloro-3-fluoro-phenyl)-1-ethyl-1H-pyrazolo[3,4-b]pyridin-5-yl]-N-methyl-isobutyramide;

2-(3,5-bis-trifluoromethyl-phenyl)-N-[4-(2,3-dichloro-phenyl)-1-ethyl-1H-pyrazolo[3,4-b]pyridin-5-yl]-N-methyl-isobutyramide;

2-(3,5-bis-trifluoromethyl-phenyl)-N-[4-(2-chloro-4-fluoro-phenyl)-1-ethyl-1H-pyrazolo[3,4-b]pyridin-5-yl]-N-methyl-isobutyramide;

2-(3,5-bis-trifluoromethyl-phenyl)-N-[4-(2-chloro-5-hydroxymethyl-phenyl)-1-ethyl-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

N-[1-acetyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-(2-methoxy-acetyl)-1H-pyrazolo[3,4-b]pyridin-5-yl]-N-methyl-isobutyramide;

2-(3,5-bis-trifluoromethyl-phenyl)-N-[1-cyclopropanecarbonyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methanesulfonyl-1H-pyrazolo[3,4-b]pyridin-5-yl]-N-methyl-isobutyramide;

2-(3,5-bis-trifluoromethyl-phenyl)-N-[1-dimethylsulfa-
moyl-4-(4-fluoro-2-methyl-phenyl)-1H-pyrazolo[3,4-b]
pyridin-5-yl]-N-methyl-isobutyramide; and
2-(3,5-bis-trifluoromethyl-phenyl)-N-[4-(4-fluoro-2-me-
thyl-phenyl)-1-methanesulfonylmethyl-1H-pyrazolo[3,4-
b]pyridin-5-yl]-N-methyl-isobutyramide.

A further embodiment of the invention provides compounds of formula I, wherein Ar is an optionally substituted five or six membered heteroaryl group and $(R^3)_n$ is 3,5-di-$CF_3$, for example the following compounds
2-(3,5-bis-trifluoromethyl-phenyl)-N-[1-ethyl-4-(4-methyl-
thiophen-3-yl)-1H-pyrazolo[3,4-b]pyridin-5-yl]-N-me-
thyl-isobutyramide and
2-(3,5-bis-trifluoromethyl-phenyl)-N-[4-(2-chloro-
thiophen-3-yl)-1-ethyl-1H-pyrazolo[3,4-b]pyridin-5-yl]-
N-methyl-isobutyramide.

A further embodiment of the invention provides compounds of formula I, wherein Ar is an optionally substituted phenyl and $(R^3)_n$ is halogen and lower alkyl, for example the following compounds
2-(3-fluoro-5-trifloromethyl-phenyl)-N-[1-ethyl-4-(4-
fluoro-2-methyl-phenyl)-1H-pyrazolo[3,4-b]pyridin-5-
yl]-N-methyl-isobutyramide and
2-(3,5-dichloro-phenyl)-N-[1-ethyl-4-(4-fluoro-2-methyl-
phenyl)-1H-pyrazolo[3,4-b]pyridin-5-yl]-N-methyl-
isobutyramide.

The present compounds of formula I and their pharmaceutically acceptable salts can be prepared by methods known in the art, described in schemes 1 to 3 and in specific examples 1 to 38 and, for example, by a process described below, which process comprises the following variants
a) reacting a compound of formula

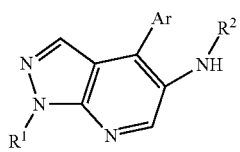

VII with a compound of formula

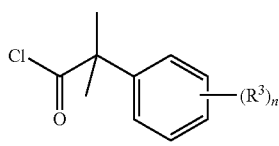

VIII to obtain a compound of formula

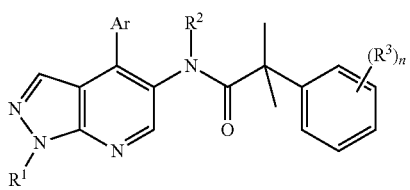

I-A wherein $R^1$, $R^2$, $R^3$, Ar and n have the significances given above, with the proviso that $R^1$ is different from hydrogen;
or b) reacting a compound of formula

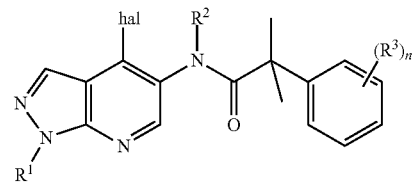

XI with a compound of formula

Ar-boronic acid to obtain a compound of formula

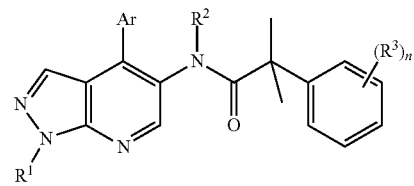

I-A wherein $R^1$, $R^2$, $R^3$, Ar and n have the significances given above, with the proviso that $R^1$ is different from hydrogen;
or c) debenzylating a compound of formula

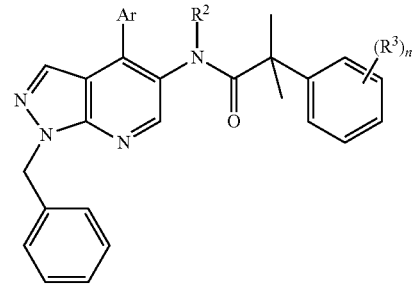

I-A-1 under high pressure of hydrogen and in the presence of Pd/C to obtain a compound of formula

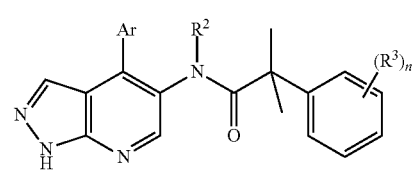

I-B wherein $R^2$, $R^3$, Ar and n have the significances given above;
or d) reacting a compound of formula

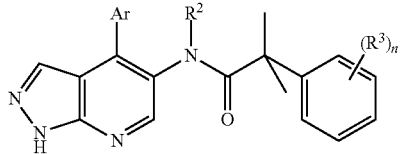

with a compound of formula

R¹—X to obtain a compound of formula

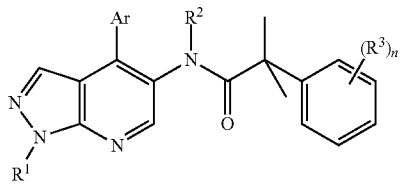

wherein R¹, R², R³, Ar and n have the significances given above, with the proviso that R¹ is different from hydrogen, and, if desired, converting the compound obtained into a pharmaceutically acceptable acid addition salt.

The following schemes 1-3 describe the processes for preparation of compounds of formula I in more detail. The starting materials are known compounds or they can be prepared according to methods known in the art. Furthermore, the preparation of intermediates is described in more detail in the experimental part.

Abbreviations:
CH₂Cl₂: dichloromethane;
DMAP: dimethylaminopyridine;
Et₃N: triethylamine;
EtOAc: ethyl acetate;
H: hexane;
mCPBA: meta-Chloroperbenzoic acid
RT: room temperature;

In general, the compounds of formula I can be prepared as follows:

General Scheme I

The preparation of derivatives of general formula I-A wherein R¹ is not a hydrogen atom and the other definitions are as described above, can be done using the following general synthetic scheme:

A Mickael addition between an amino pyrrazole II and 2-ethoxymethylene-malonic acid diethyl ester at 120° C. give the intermediate III which readily undergo an intramolecular cyclization with POCl₃ at 130° C. yielding IV. A Suzuki coupling with an aryl boronic acid catalized by palladium, particularly Pd(PPh₃)₄ give the compound of formula V. Hydrolysis of the ester under basic conditions, for example NaOH, followed by a Curtius rearrangement with DPPA in presence of tBuOH lead to compound VI. An alkylation with R²—X and NaH followed by boc-deprotection with TFA give a compound of formula VII, which is finally coupled with an acid chloride VIII to give a compound of formula I-A.

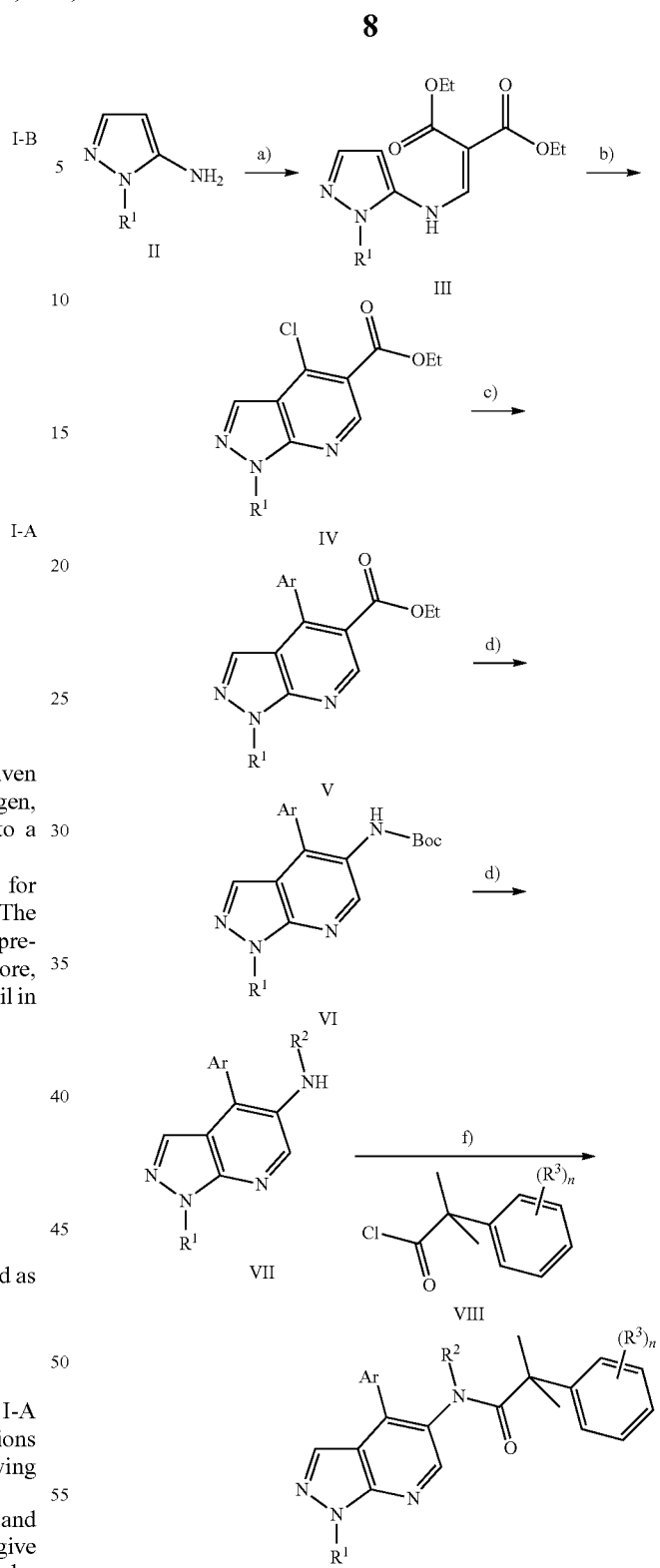

a) 2-Ethoxymethylene-malonic acid diethyl ester. b) POCl₃. c) Ar—B(OH)₂, Pd(PPH₃)₄. d) i. NaOH; ii. DPPA, tBuOH. e) i. NaH, R²—X; ii. TFA. f) VIII, iPr₂NEt.

General Scheme II

Alternatively, derivatives of type I-A wherein R¹ is not a hydrogen atom and the other definitions are as described above, can be prepared via the following route: After hydrolysis of the intermediate IV under basic conditions, for instance with NaOH, a Curtius rearrangement is performed with DPPA and tBuOH to form compound IX. Deprotonation with preferably NaH and alkylation with $R^2$—X, followed by deprotection with TFA lead to a compound of formula X. The amine X is then coupled with an acid chloride of formula VIII in the presence of a base, such as $iPr_2Net$, to give an amide of formula XI. Finally, a Suzuki coupling with an aryl boronic acid give final derivatives of formula I-A.

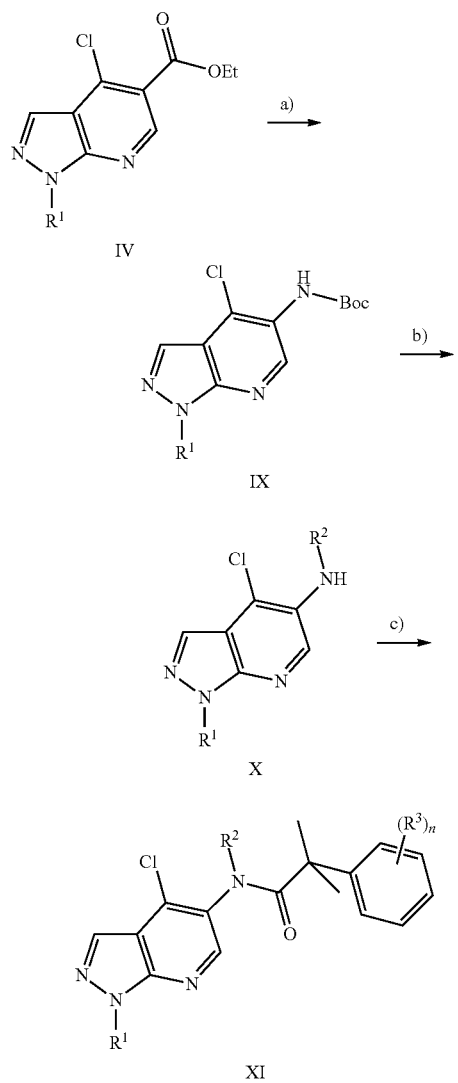

a) i. NaOH; ii. DPPA, tBuOH; b) i. NaH, $R^2$—X; ii. TFA. c) VIII, $iPr_2NEt$ d) $ArB(OH)_2$, $Pd(PPh_3)_4$

General Scheme III

Finally, a third route is used to prepared derivatives of formula I-B wherein $R^1$ is an hydrogen and the other definitions are as described above. Additionally, compounds of the type I-B can be converted into final compounds of general formula I.

Compounds I-A-1, wherein $R^1$ is benzyl and the other definitions are as described above, is debenzylated under high pressure of hydrogen (preferably 10 bars) and in the presence of Pd/C to give a compound of formula I-B. Deprotonation of compounds I-B with NaH follwed by addition of $R^1$—X give derivatives of formula I.

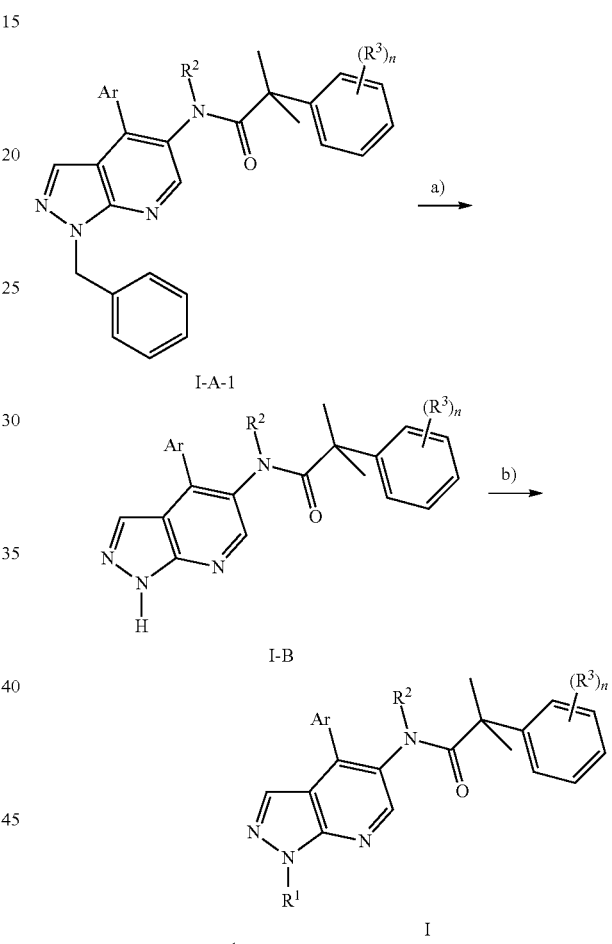

a) Pd/C, $H_2$ 10 bars b) NaH, $R^1$—X

As mentioned earlier, the compounds of formula I and their pharmaceutically usable addition salts possess valuable pharmacological properties. It has been found that the compounds of the present invention are antagonists of neurokinin 3 (NK-3) and neurokin 1 (NK-1) receptors. The compounds were investigated in accordance with the tests given hereinafter.

NK1

The affinity of test compounds for the NK1 receptor was evaluated at human NK1 receptors in CHO cells infected with the human NK1 receptor (using the Semliki virus expression system) and radiolabelled with [$^3$H]substance P (final concentration 0.6 nM). Binding assays were performed in HEPES buffer (50 mM, pH 7.4) containing BSA (0.04%)

leupeptin (16.8 μg/ml), MnCl$_2$ (3 mM) and phosphoramidon (2 μM). Binding assays consisted of 250 μl of membrane suspension (approximately 1.5 μg/well in a 96 well plate), 0.125 μl of buffer of displacing agent and 125 μl of [$^3$H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 3×1 ml washes of HEPES buffer (50 mM, pH 7.4). The radioactivity retained on the filters was measured by scintillation counting. All assays were performed in duplicate in at least 2 separate experiments.

NK3

Recombinant human NK$_3$ (hNK3) receptor affinity was determined in a 96 well plate assay, using [$^3$H]SR142801 (final concentration 0.3 nM) to radiolabel the hNK3 receptor in the presence of 10 concentrations of competing compound or buffer. Non specific binding was determined using 10 μM SB222200. Assay buffer consisted of Tris-HCl (50 mM, pH 7.4), BSA (0.1%), MnCl$_2$ (4 mM) and phosphoramidon (1 μM). Membrane preparations of hNK3 receptors (approximately 2.5 μg/well in a 96 well plate) were used to initiate the incubation for 90 min at room temperature. This assay was terminated by rapid filtration under vacuum through GF/C filters, presoaked for 90 min with PEI (0.3%), with 3×0.5 ml washes of ice-cold Tris buffer (50 mM, pH 7.4) containing 0.1% BSA. The radioactivity retained on the filters was measured by scintillation counting. All assays were performed in duplicate in at least two separate experiments.

The activity of the present compounds is described in the table below:

| Example No. | Ki NK1 μM | Ki NK3 μM |
| --- | --- | --- |
| 1 | 0.0012 | 0.0327 |
| 2 | 0.0011 | 0.0257 |
| 3 | 0.0006 | 0.0229 |
| 4 | 0.0004 | 0.0868 |
| 5 | 0.006 | 0.1996 |
| 6 | 0.0009 | 0.0068 |
| 7 | 0.0008 | 0.0189 |
| 8 | 0.0017 | 0.4834 |
| 9 | 0.0102 | 0.779 |
| 10 | 0.0025 | 0.532 |
| 11 | 0.0013 | 0.077 |
| 12 | 0.0007 | 0.0414 |
| 13 | 0.0079 | 0.1602 |
| 14 | 0.0016 | 0.0387 |
| 15 | 0.0007 | 0.2084 |
| 16 | 0.0086 | 0.3727 |
| 17 | 0.0042 | 0.3553 |
| 18 | 0.0000 | 0.0453 |
| 19 | 0.0003 | 0.0138 |
| 20 | 0.0016 | 0.2094 |
| 21 | 0.092 | 0.0012 |
| 22 | 0.0025 | 0.0048 |
| 23 | 0.0049 | 0.9793 |
| 24 | 0.036 | 0.0007 |
| 25 | 0.522 | |
| 26 | 0.0042 | 0.0942 |
| 27 | 0.0026 | 0.0351 |
| 28 | 0.0016 | 0.0273 |
| 29 | 0.0345 | 0.308 |
| 30 | 0.0124 | 0.8752 |
| 31 | 0.0012 | 0.0129 |
| 32 | 0.0019 | 0.0284 |
| 33 | 0.0016 | 0.0099 |
| 34 | | 0.0395 |
| 35 | | 0.0939 |
| 36 | 0.0006 | 0.0151 |
| 37 | 0.0075 | 0.0785 |
| 38 | 0.0011 | 0.008 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. gelatingelatinLactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of formula I can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention. All temperatures are given in degrees Celsius.

EXPERIMENTAL PROCEDURES

General Procedure I

Suzuki Coupling Between Intermediate XI-1 and an Aryl Boronic Acid

To a stirred solution of 2-(3,5-bis-trifluoromethyl-phenyl)-N-(4-chloro-1-ethyl-1H-pyrazolo[3,4-b]pyridin-5-yl)-N-methyl-isobutyramide (intermediate XI-1, 0.1 mmol) in EtOH (2 mL) and toluene (4 mL) was added the aryl boronic acid (0.15 mmol), $Pd(PPh_3)_4$ (0.01 mmol) and an aqueous solution of $NaHCO_3$ (1M, 0.2 mmol). The reaction mixture was heated at 80° C. until completion of the reaction (assessed by LCMS or TLC). The mixture was then poured on EtOAc (10 mL) and washed with aqueous NaOH (0.1 M, 10 mL). The organic phase was dried over $Na_2SO_4$, concentrated under vacuo and then purification by preparative HPLC afforded the desired compound.

General Procedure II

Amid Formation Between the Intermediate VII-1 and Acid Chloride VIII

To a stirred solution of [1-ethyl-4-(4-fluoro-2-methyl-phenyl)-1H-pyrazolo[3,4-b]pyridin-5-yl]-methyl-amine (intermediate VII-1, 0.1 mmol) in $CH_2Cl_2$ (5 mL) was added $Et_3N$ (0.2 mmol) and an acid chloride of formula VIII. The reaction mixture was heated at 35° C. until completion of the reaction (assessed by LCMS or TLC), and then washed with $H_2O$. The organic phase was dried over $Na_2SO_4$, concentrated under vacuo and then purification by preparative HPLC afforded the desired compound.

General Procedure III

Reaction of the Intermediate I-B-1 with Various Electrophile (Alkyl-Halides, Acid Chloride, Sulfonyl Chloride or Sulfamyl Chlorid To solution of 2-(3,5-bis-trifluoromethyl-phenyl)-N-[4-(4-fluoro-2-methyl-phenyl)-1H-pyrazolo[3,4-b]pyridin-5-yl]-N-methyl-isobutyramide (0.1 mmol) in DMF (4 mL) at 0° C. was added NaH (0.12 mmol). After 30 minutes, an alkyl halide, acid chloride sulfonyl chloride or sulfamid chloride of formula $R^1$—X (0.11 mmol) was added and the temperature was raised to RT until competion of the reaction (assessed by LCMS or TLC). The reaction mixture was poured into EtOAc (30 mL) and then washed with $H_2O$ (25 mL). The organic phase was dried over $Na_2SO_4$, concentrated under vacuo and then purification by preparative HPLC afforded the desired compound.

Intermediates of Formula VII

VII-1

[1-Ethyl-4-(4-fluoro-2-methyl-phenyl)-1H-pyrazolo[3,4-b]pyridin-5-yl]-methyl-amine

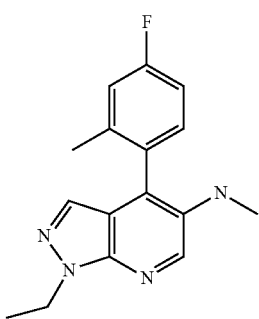

VII-1 a) 2-[(2-Ethyl-2H-pyrazol-3-ylamino)-methylene]-malonic acid diethyl ester

To 2-ethyl-2H-pyrazol-3-ylamine (5.6 g, 0.050 mol) was added 2-ethoxymethylene-malonic acid diethyl ester (10.1 mL, 0.050 mol) and the mixture was heated at 120° C. for 4 hours. After cooling down to RT, the crude mixture was purified by column chromatography ($SiO_2$, EtOAc/Heptane 1/1) to give 12.25 g (86%) of the title compound as a yellow oil. ES-MS m/e: 282.4 (M+H$^-$).

b) 4-Chloro-1-ethyl-1H-pyrazolo[3,4-b]pyridine-5-carboxylic acid ethyl ester

A solution of 2-[(2-ethyl-2H-pyrazol-3-ylamino)-methylene]-malonic acid diethyl ester (11.75 g, 0.041 mol) in $POCl_3$ (70 mL) was heated at reflux (135° C.) for 8 hours. The excess of POCl₃ were distilled off and the reaction mixture cooled to 0° C., before careful addition of water (100 mL) and then aqueous NaOH (3N) until pH reached 7. The product was extracted with CH₂Cl₂ several times, and the combined orgnic phase were dried over Na₂SO₄ and concentrated under vacuo. Column chromatography (SiO₂, EtOAc/Heptane 1/5) afforded 7.22 g (69%) of the title product as a white solid. ES-MS m/e: 254.2 (M+H⁺).

c) 1-Ethyl-4-(4-fluoro-2-methyl-phenyl)-1H-pyrazolo[3,4-b]pyridine-5-carboxylic acid ethyl ester A solution of 4-chloro-1-ethyl-1H-pyrazolo[3,4-b]pyridine-5-carboxylic acid ethyl ester (3.6 g, 0.014 mol) in toluene (80 mL) and EtOH (40 mL) was degassed 3 times before Pd(PPh₃)₄ (0.49 g, 0.425 mmol), 4-fluoro-2-methylphenylboronic acid (2.62 g, 0.017 mol) and an aqueous solution of Na₂CO₃ (2N, 14.2 mL, 0.028 mol) were added. The reaction mixture was stirred at 70° C. for 15 hours, cooled down to RT, filtered and the volatiles evaporated under vacuo. The residue was taken up in EtOAc and washed with aqueous NaOH (1N). The organic phase was dried over Na₂SO₄, concentrated under vacuo, before a purification on column chromatography (SiO₂, EtOAc/Heptane, 1/3) yielded 3.6 g (77%) of the title compound as a colorless oil. ES-MS m/e: 328.2 (M+H⁺).

d) [1-Ethyl-4-(4-fluoro-2-methyl-phenyl)-1H-pyrazolo[3,4-b]pyridin-5-yl]-carbamic acid tert-butyl ester To a solution of 1-ethyl-4-(4-fluoro-2-methyl-phenyl)-1H-pyrazolo[3,4-b]pyridine-5-carboxylic acid ethyl ester (3.6 g, 0.011 mol) in EtOH (20 mL) and THF (20 mL) was added an aqueous solution of NaOH (1N, 16.5 mL, 0.016 mol) and the mixture was heated at 50° C. for 3 hours. After cooling down to RT, the mixture was acidified with aqueous HCl (1N) until pH reached 3 and the product extracted with EtOAc. The combined organic phases were dried over Na₂SO₄ and concentrated to give the crude acid which was used directly in the next step without further purification. The residue was taken up in THF (90 mL) before Et₃N (1.49 mL, 0.0107 mol), DPPA (diphenyl phosphorazidate, 2.94 g, 0.0107 mol) and tBuOH (4.0 mL, 0.0428 mol) were added. The reaction mixture was heated at 60° C. for 7 hours, volatiles were then partially evaporated, and the concentrated solution poured onto EtOAc (200 mL) and washed with H₂O. The organic layer was dried over Na₂SO₄, and purification by column chromatography (SiO₂, EtOAc/Heptane 1/4) yielded 2.6 g (65%) of the title compound as a white solid. ES-MS m/e: 371.2 (M+H⁺).

e) [1-Ethyl-4-(4-fluoro-2-methyl-phenyl)-1H-pyrazolo[3,4-b]pyridin-5-yl]-methyl-amine To a solution of [1-ethyl-4-(4-fluoro-2-methyl-phenyl)-1H-pyrazolo[3,4-b]pyridin-5-yl]-carbamic acid tert-butyl ester (2.6 g, 7.02 mmol) in DMF (50 mL) at 0° C. was added NaH (0.44 g, 50% purity, 9.12 mmol). After 20 minutes, iodomethane (1.49 g, 10.5 mmol) was added and the temperature raised to RT. The reaction was quenched by addition of H₂O and the product extracted with EtOAc. The combined organic phases were dried over Na₂SO₄, and concentrated under vacuo to give a crude intermediate which was used directly in the next step without further purification. This residue as dissolved in CH₂Cl₂ (30 mL) and TFA (8 mL) was added. The reaction mixture was heated at 40° C. for 2 hours, diluted with CH₂Cl₂ (100 mL) and aqueous NaOH (1N) was added until pH reached 8. The organic phase was dried over Na₂SO₄, concentrated under vacuo to give the title product 1.95 g with high purity (no further purification needed) (99%) as a light yellow solid. ES-MS m/e: 285.1 (M+H⁺).

Intermediates of Formula XI

XI-1

2-(3,5-Bis-trifluoromethyl-phenyl)-N-(4-chloro-1-ethyl-1H-pyrazolo[3,4-b]pyridin-5-yl)-N-methyl-isobutyramide

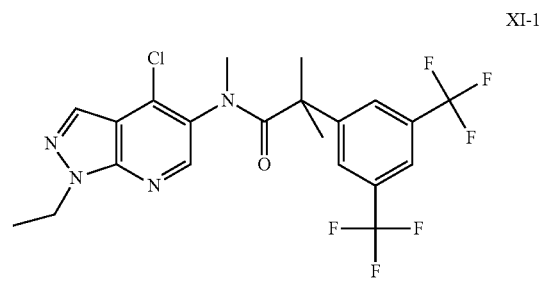 [SMILES: CCn1ncc2c(Cl)c(N(C)C(=O)C(C)(C)c3cc(C(F)(F)F)cc(C(F)(F)F)c3)cnc21]

a) (4-Chloro-1-ethyl-1H-pyrazolo[3,4-b]pyridin-5-yl)-carbamic acid tert-butyl ester To a solution of 4-chloro-1-ethyl-1H-pyrazolo[3,4-b]pyridine-5-carboxylic acid ethyl ester (described herein above, 3.5 g, 0.0138 mol) in EtOH (20 mL) and THF (20 mL) was added an aqueous solution of NaOH (1N, 20.7 mL, 0.0207 mol) and the mixture was heated at 35° C. for 2 hours. After cooling down to RT, the mixture was acidified with aqueous HCl (1N) until pH reached 4 and the product extracted with EtOAc. The combined organic phases were dried over Na₂SO₄ and concentrated to give the crude acid which was used directly in the next step without further purification. The residue was taken up in THF (90 mL) before Et₃N (1.85 mL, 0.0133 mol), DPPA (diphenyl phosphorazidate, 3.66 g, 0.0133 mol) and tBuOH (5.0 mL, 0.0532 mol) were added. The reaction mixture was heated at 60° C. for 6 hours, volatiles were then partially evaporated, and the concentrated solution poured onto EtOAc (200 mL) and washed with H₂O (2 times 150 mL). The organic layer was dried over Na₂SO₄, and purification by column chromatography (SiO₂, EtOAc/Heptane 1/4) yielded 3.3 g (84%) of the title compound as a white waxy solid. ES-MS m/e: 297.2 (M+H⁺).

b) (4-Chloro-1-ethyl-1H-pyrazolo[3,4-b]pyridin-5-yl)-methyl-amine

To a solution of (4-chloro-1-ethyl-1H-pyrazolo[3,4-b]pyridin-5-yl)-carbamic acid tert-butyl ester (3.3 g, 11.1 mmol) in DMF (50 mL) at 0° C. was added NaH (0.694 g, 50% purity, 14.5 mmol). After 20 minutes, iodomethane (2.37 g, 16.7 mmol) was added and the temperature raised to RT. The reaction was quenched by addition of H₂O and the product extracted with EtOAc. The combined organic phases were dried over Na₂SO₄, and concentrated under vacuo to give a crude intermediate which was used directly in the next step without further purification. This residue as dissolved in CH₂Cl₂ (50 mL) and TFA (10 mL) was added. The reaction mixture was heated at 30° C. for 3 hours, diluted with CH₂Cl₂

(100 mL) and aqueous NaOH (1N) was added until pH reached 8. The organic phase was dried over Na$_2$SO$_4$, concentrated under vacuo to give the title product 2.24 g with high purity (no further purification needed) (96%) as a light yellow solid. ES-MS m/e: 211.2 (M+H$^+$).

c) 2-(3,5-Bis-trifluoromethyl-phenyl)-N-(4-chloro-1-ethyl-1H-pyrazolo[3,4-b]pyridin-5-yl)-N-methyl-isobutyramide To a solution of (4-chloro-1-ethyl-1H-pyrazolo[3,4-b]pyridin-5-yl)-methyl-amine (2.24 g, 10.63 mmol) in CH$_2$Cl$_2$ (50 mL) was added iPr$_2$NEt (3.69 mL, 21.20 mmol) and 2-(3,5-Bis-trifluoromethyl-phenyl)-2-methyl-propionyl chloride (described in *J. Org. Chem*, 2006, 71, 2000-2008, 4.38 g, 13.70 mmol). The reaction mixture was heated at 40° C. for 2 hours, diluted with CH$_2$Cl$_2$ (100 mL), and washed with H$_2$O. The organic phase was dried over Na$_2$SO$_4$, concentrated under vacuo, and column chromatography (SiO$_2$, EtOAc/Heptane 1/4) afforded 4.96 g (95%) of the title compound as a light yellow solid. ES-MS m/e: 493.2 (M+H$^+$).

Intermediates of Formula I-B

I-B-1

2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide

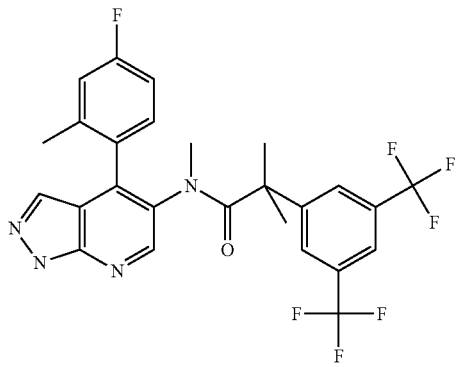

I-B-1 a) 2-[(2-Benzyl-2H-pyrazol-3-ylamino)-methylene]-malonic acid diethyl ester

To 2-benzyl-2H-pyrazol-3-ylamine (5.0 g, 0.0289 mol) was added 2-ethoxymethylene-malonic acid diethyl ester (5.78 mL, 0.0289 mol) and the mixture was heated at 120° C. for 4 hours. After cooling down to RT, the crude mixture was purified by column chromatography (SiO$_2$, EtOAc/Heptane 1/1) to give 7.44 g (75%) of the title compound as a light yellow oil.

b) 1-Benzyl-4-chloro-1H-pyrazolo[3,4-b]pyridine-5-carboxylic acid ethyl ester

A solution of 2-[(2-benzyl-2H-pyrazol-3-ylamino)-methylene]-malonic acid diethyl ester (7.0 g, 0.020 mol) in POCl$_3$ (50 mL) was heated at reflux (130° C.) for 8 hours. The excess of POCl$_3$ were distilled off and the reaction mixture cooled to 0° C., before careful addition of water (100 mL) and then aqueous NaOH (3N) until pH reached 7. The product was extracted with CH$_2$Cl$_2$ several times, and the combined orgnic phase were dried over Na$_2$SO$_4$ and concentrated under vacuo. Column chromatography (SiO$_2$, EtOAc/Heptane 1/6) afforded 4.10 g (65%) of the title product as a white solid.

c) 1-Benzyl-4-(4-fluoro-2-methyl-phenyl)-1H-pyrazolo[3,4-b]pyridine-5-carboxylic acid ethyl ester A solution of 1-benzyl-4-chloro-1H-pyrazolo[3,4-b]pyridine-5-carboxylic acid ethyl ester (4.56 g, 0.0144 mol) in toluene (80 mL) and EtOH (40 mL) was degassed 3 times before Pd(PPh$_3$)$_4$ (0.834 g, 0.722 mmol), 4-fluoro-2-methylphenylboronic acid (2.67 g, 0.0173 mol) and an aqueous solution of Na$_2$CO$_3$ (2N, 14.4 mL, 0.0288 mol) were added. The reaction mixture was stirred at 75° C. for 15 hours, cooled down to RT, filtered and the volatiles evaporated under vacuo. The residue was taken up in EtOAc and washed with aqueous NaOH (1N). The organic phase was dried over Na$_2$SO$_4$, concentrated under vacuo, before a purification on column chromatography (SiO$_2$, EtOAc/Heptane, 1/4) yielded 4.74 g (84%) of the title compound as a colorless solid.

d) [1-Benzyl-4-(4-fluoro-2-methyl-phenyl)-1H-pyrazolo[3,4-b]pyridin-5-yl]-carbamic acid tert-butyl ester To a solution of 1-benzyl-4-(4-fluoro-2-methyl-phenyl)-1H-pyrazolo[3,4-b]pyridine-5-carboxylic acid ethyl ester (4.0 g, 10.3 mmol) in EtOH (20 mL) and THF (20 mL) was added an aqueous solution of NaOH (1N, 20 mL, 20.0 mmol) and the mixture was heated at 50° C. for 3 hours. After cooling down to RT, the mixture was acidified with aqueous HCl (1N) until pH reached 3 and the product extracted with EtOAc. The combined organic phases were dried over Na$_2$SO$_4$ and concentrated to give the crude acid which was used directly in the next step without further purification. The residue was taken up in THF (20 mL) before Et$_3$N (1.42 mL, 10.3 mmol), DPPA (diphenyl phosphorazidate, 2.83 g, 10.3 mmol) and tBuOH (3.85 mL, 41.1 mmol) were added. The reaction mixture was heated at 60° C. for 7 hours, volatiles were then partially evaporated, and the concentrated solution poured onto EtOAc (200 mL) and washed with H$_2$O. The organic layer was dried over Na$_2$SO$_4$, and purification by column chromatography (SiO$_2$, EtOAc/Heptane 1/5) yielded 2.6 g (58%) of the title compound as a white solid.

e) [1-Benzyl-4-(4-fluoro-2-methyl-phenyl)-1H-pyrazolo[3,4-b]pyridin-5-yl]-methyl-amine To a solution of [1-benzyl-4-(4-fluoro-2-methyl-phenyl)-1H-pyrazolo[3,4-b]pyridin-5-yl]-carbamic acid tert-butyl ester (2.6 g, 6.01 mmol) in DMF (50 mL) at 0° C. was added NaH (0.462 g, 50% purity, 9.62 mmol). After 20 minutes, iodomethane (1.54 g, 10.8 mmol) was added and the temperature raised to RT. The reaction was quenched by addition of H$_2$O and the product extracted with EtOAc. The combined organic phases were dried over Na$_2$SO$_4$, and concentrated under vacuo to give a crude intermediate which was used directly in the next step without further purification. This residue as dissolved in CH$_2$Cl$_2$ (50 mL) and TFA (15 mL) was added. The reaction mixture was heated at 30° C. for 2 hours, diluted with CH$_2$Cl$_2$ (100 mL) and aqueous NaOH (1N) was added until pH reached 8. The organic phase was dried over Na$_2$SO$_4$, concentrated under vacuo to give the title product 2.24 g (97%) with high purity (no further purification needed) as a light yellow solid. ES-MS m/e: 347.3 (M+H⁺).

f) N-[1-Benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide To a solution of [1-benzyl-4-(4-fluoro-2-methyl-phenyl)-1H-pyrazolo[3,4-b]pyridin-5-yl]-methyl-amine (2.125 g, 6.13 mmol) in CH$_2$Cl$_2$ (30 mL) was added iPr$_2$NEt (2.14 mL, 12.3 mmol) and 2-(3,5-Bis-trifluoromethyl-phenyl)-2-methyl-propionyl chloride (described in *J. Org. Chem*, 2006, 71, 2000-2008, 2.93 g, 9.20 mmol). The reaction mixture was heated at 40° C. for 2 hours, diluted with CH$_2$Cl$_2$ (100 mL), and washed with H$_2$O. The organic phase was dried over Na$_2$SO$_4$, concentrated under vacuo, and column chromatography (SiO$_2$, EtOAc/Heptane 1/4) afforded 3.2 g (83%) of the title compound as a white foam. ES-MS m/e: 629.2 (M+H⁺).

e) 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide To a solution of N-[1-benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide (0.40 g, 0.636 mmol) in MeOH (12 mL) was added Pd/C (120 mg) and aqueous HCl (0.078 mL, 37% in H$_2$O) and was put under hydrogen pressure at 10 bars. The reaction mixture was stirred at 60° C. for 20 hours before volatiles were removed, pH adjusted to 8 with aqueous NaOH, and the product extracted with EtOAc. The combined organic phases were dried over Na$_2$SO$_4$, and purification by column chromatography (SiO$_2$, EtOAc/Heptane 1/1) yielded 141 mg (41%) of the title compound as a white powder. ES-MS m/e: 539.2 (M+H⁺).

Example 1

2-(3,5-Bis-trifluoromethyl-phenyl)-N-(1-ethyl-4-o-tolyl-1H-pyrazolo[3,4-b]pyridin-5-yl)-N-methyl-isobutyramide

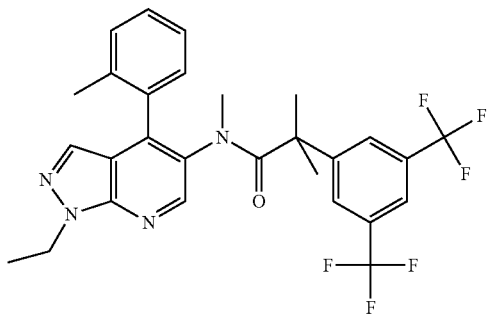

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: o-Tolylboronic acid (commercially available)
ES-MS m/e: 549.3 (M+H⁺).

Example 2

2-(3,5-Bis-trifluoromethyl-phenyl)-N-[1-ethyl-4-(4-fluoro-2-methyl-phenyl)-1H-pyrazolo[3,4-b]pyridin-5-yl]-N-methyl-isobutyramide

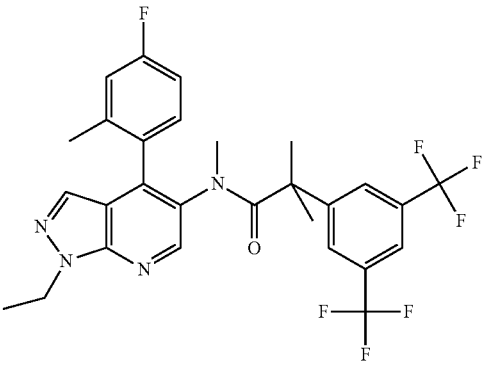

Amid coupling according to general procedure II:
Pyrrazolo-pyridine intermediate: [1-Ethyl-4-(4-fluoro-2-methyl-phenyl)-1H-pyrazolo[3,4-b]pyridin-5-yl]-methyl-amine (VII-1)
Acid chlorid: 2-(3,5-Bis-trifluoromethyl-phenyl)-2-methyl-propionyl chloride (preparation described *J. Org. Chem*, 2006, 71, 2000-2008)
ES-MS m/e: 567.3 (M+H⁺).

Example 3

2-(3,5-Bis-trifluoromethyl-phenyl)-N-[4-(2-chloro-phenyl)-1-ethyl-1H-pyrazolo[3,4-b]pyridin-5-yl]-N-methyl-isobutyramide

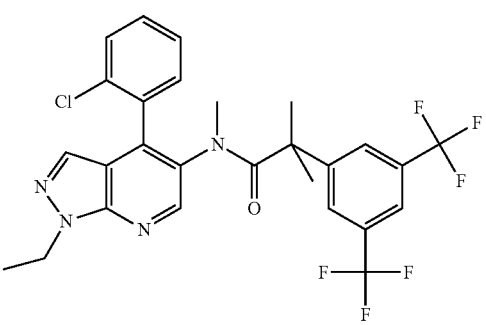

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: 2-Chlorophenylboronic acid (commercially available) ES-MS m/e: 569.2 (M+H⁺).

Example 4

2-(3,5-Bis-trifluoromethyl-phenyl)-N-[4-(3,4-dichloro-phenyl)-1-ethyl-1H-pyrazolo[3,4-b]pyridin-5-yl]-N-methyl-isobutyramide

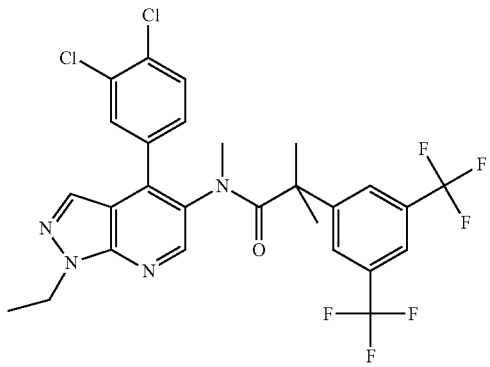 [SMILES: CCn1ncc2c(-c3ccc(Cl)c(Cl)c3)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 3,4-Dichlorophenylboronic acid (commercially available)

ES-MS m/e: 603.1 (M+H$^+$).

Example 5

2-(3,5-Bis-trifluoromethyl-phenyl)-N-[1-ethyl-4-(4-fluoro-2-methyl-phenyl)-1H-pyrazolo[3,4-b]pyridin-5-yl]-isobutyramide

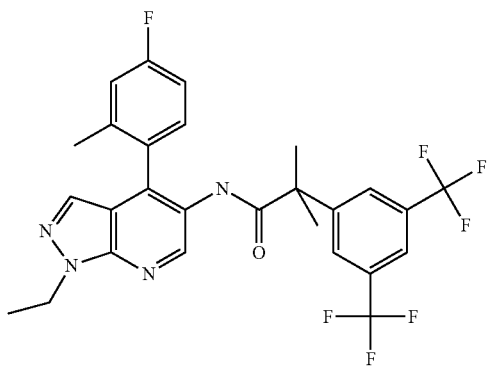

[1-Ethyl-4-(4-fluoro-2-methyl-phenyl)-1H-pyrazolo[3,4-b]pyridin-5-yl]-carbamic acid tert-butyl ester (preparation described above in course of the synthesis of VII-1) was boc-deprotected upon treatment with TFA at RT in CH$_2$Cl$_2$ to yield the free primary amine which was directly coupled with the acid chloride 2-(3,5-Bis-trifluoromethyl-phenyl)-2-methyl-propionyl chloride using the general procedure I to give the tile product. ES-MS m/e: 553.3 (M+H$^+$).

Example 6

2-(3,5-Bis-trifluoromethyl-phenyl)-N-[1-(2,2-difluoro-ethyl)-4-(4-fluoro-2-methyl-phenyl)-1H-pyrazolo[3,4-b]pyridin-5-yl]-N-methyl-isobutyramide

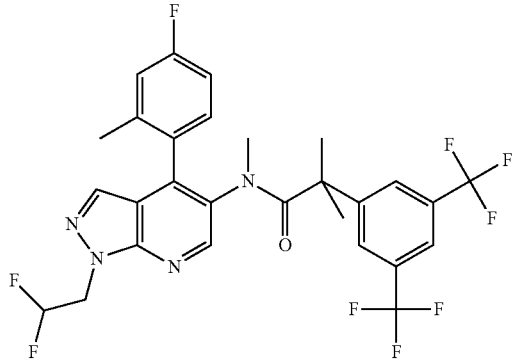 [SMILES: Cc1cc(F)ccc1-c1c(N(C)C(=O)C(C)(C)c2cc(C(F)(F)F)cc(C(F)(F)F)c2)cnc2c1cnn2CC(F)F]

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and 2,2-Difluoroethyl triflate (commercially available) ES-MS m/e: 603.2 (M+H$^+$).

Example 7

2-(3,5-Bis-trifluoromethyl-phenyl)-N-[4-(4-fluoro-2-methyl-phenyl)-1-methyl-1H-pyrazolo[3,4-b]pyridin-5-yl]-N-methyl-isobutyramide

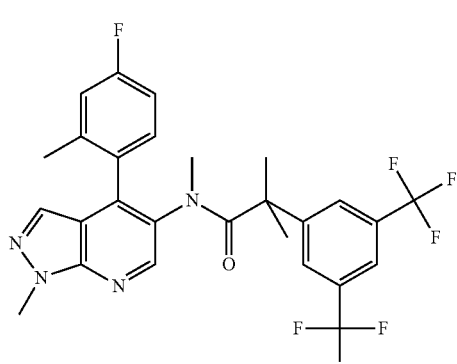

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and iodomethane (commercially available) ES-MS m/e: 553.3 (M+H$^+$).

Example 8

2-(3,5-Bis-trifluoromethyl-phenyl)-N-[4-(2,4-difluoro-phenyl)-1-ethyl-1H-pyrazolo[3,4-b]pyridin-5-yl]-N-methyl-isobutyramide

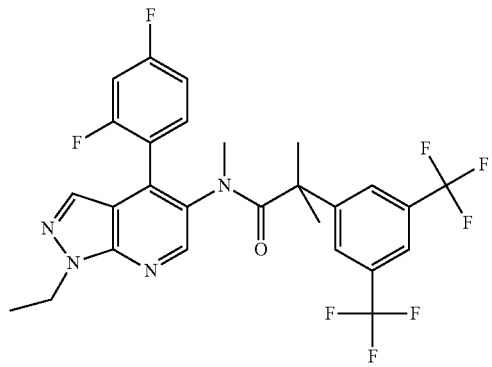 [SMILES: CCn1ncc2c(-c3ccc(F)cc3F)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2,4-Difluorophenylboronic acid (commercially available) ES-MS m/e: 571.3 (M+H$^+$).

Example 9

22-(3,5-Bis-trifluoromethyl-phenyl)-N-[4-(2,3-difluoro-phenyl)-1-ethyl-1H-pyrazolo[3,4-b]pyridin-5-yl]-N-methyl-isobutyramide

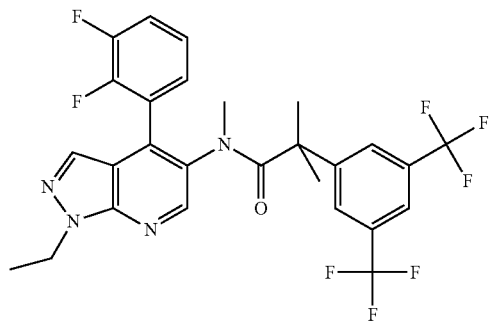 [SMILES: CCn1ncc2c(-c3cccc(F)c3F)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2,3-Difluorophenylboronic acid (commercially available) ES-MS m/e: 571.3 (M+H$^+$).

Example 10

2-(3,5-Bis-trifluoromethyl-phenyl)-N-(1-ethyl-4-phenyl-1H-pyrazolo[3,4-b]pyridin-5-yl)-N-methyl-isobutyramide

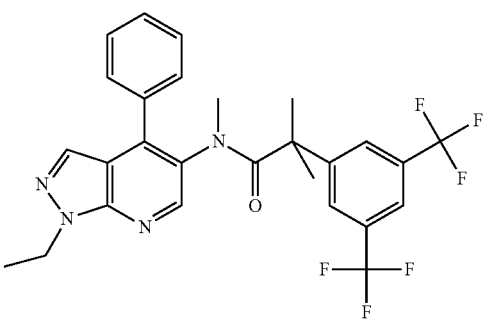 [SMILES: CCn1ncc2c(-c3ccccc3)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: Phenylboronic acid (commercially available) ES-MS m/e: 535.1 (M+H$^+$).

Example 11

N-[1-Benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide

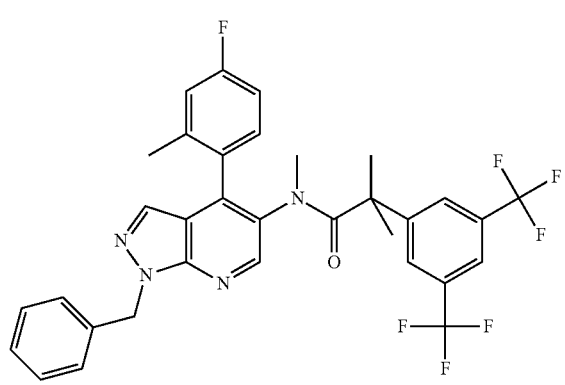 [SMILES: Cc1cc(F)ccc1-c1c(N(C)C(=O)C(C)(C)c2cc(C(F)(F)F)cc(C(F)(F)F)c2)cnc2c1cnn2Cc1ccccc1]

This compound is a precursor of the intermediate I-B-1 and its full synthesis is described there. ES-MS m/e: 627.7 (M+H$^+$).

Example 12

2-(3,5-Bis-trifluoromethyl-phenyl)-N-[1-ethyl-4-(4-fluoro-2-methoxy-phenyl)-1H-pyrazolo[3,4-b]pyridin-5-yl]-N-methyl-isobutyramide

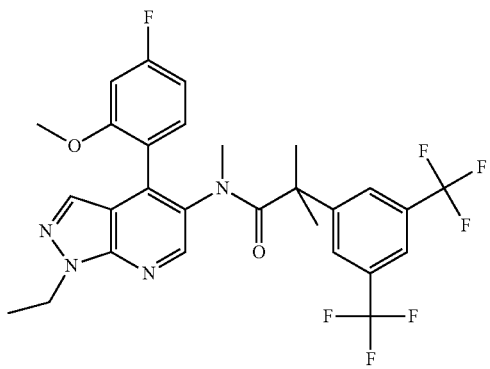

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: 4-Fluoro-2-methoxyphenylboronic acid (commercially available) ES-MS m/e: 583.2 (M+H$^+$).

Example 13

2-(3,5-Bis-trifluoromethyl-phenyl)-N-[1-ethyl-4-(5-fluoro-2-methyl-phenyl)-1H-pyrazolo[3,4-b]pyridin-5-yl]-N-methyl-isobutyramide

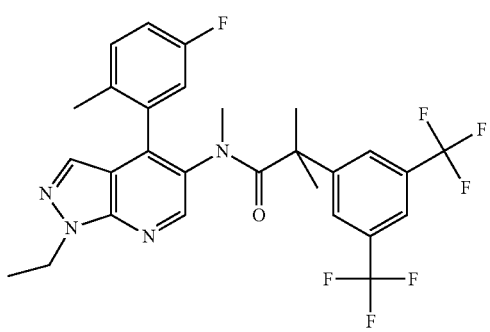 [SMILES: CCn1ncc2c(-c3cc(F)ccc3C)c(N(C)C(=O)C(C)(C)c3cc(C(F)(F)F)cc(C(F)(F)F)c3)cnc21]

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: (5-Fluoro-2-methylphenyl)boronic acid (commercially available)
ES-MS m/e: 567.2 (M+H$^+$).

Example 14

2-(3,5-Bis-trifluoromethyl-phenyl)-N-[4-(2-chloro-3-fluoro-phenyl)-1-ethyl-1H-pyrazolo[3,4-b]pyridin-5-yl]-N-methyl-isobutyramide

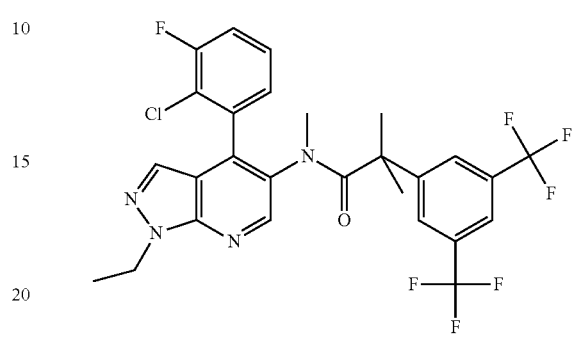

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: (2-Chloro-3-fluorophenyl)boronic acid (commercially available) ES-MS m/e: 587.1 (M+H$^+$).

Example 15

2-(3,5-Bis-trifluoromethyl-phenyl)-N-[1-ethyl-4-(2-methoxy-phenyl)-1H-pyrazolo[3,4-b]pyridin-5-yl]-N-methyl-isobutyramide

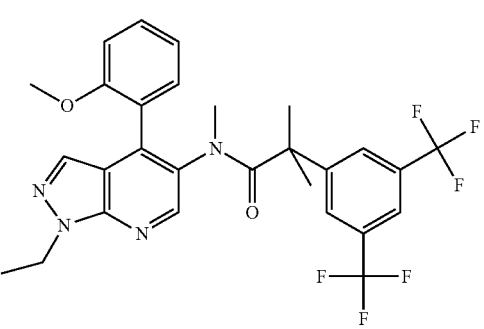 [SMILES: CCn1ncc2c(-c3ccccc3OC)c(N(C)C(=O)C(C)(C)c3cc(C(F)(F)F)cc(C(F)(F)F)c3)cnc21]

Suzuki coupling according to general procedure I:
Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)
Boronic acid: 2-Methoxyphenylboronic acid (commercially available)
ES-MS m/e: 565.2 (M+H$^+$).

Example 16

2-(3,5-Bis-trifluoromethyl-phenyl)-N-[1-ethyl-4-(4-methoxy-2-methyl-phenyl)-1H-pyrazolo[3,4-b]pyridin-5-yl]-N-methyl-isobutyramide

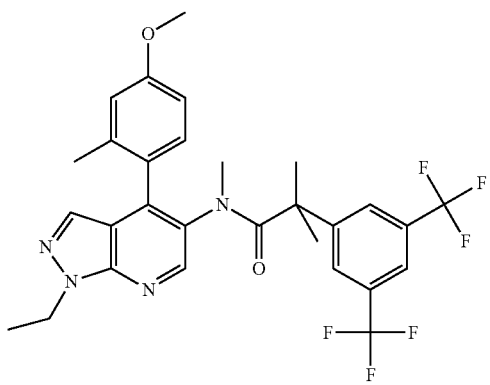 [SMILES: CCn1ncc2c(-c3ccc(OC)cc3C)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 4-Methoxy-2-methylphenylboronic acid (commercially available)

ES-MS m/e: 579.2 (M+H$^+$).

Example 17

2-(3,5-Bis-trifluoromethyl-phenyl)-N-[4-(3-chloro-phenyl)-1-ethyl-1H-pyrazolo[3,4-b]pyridin-5-yl]-N-methyl-isobutyramide

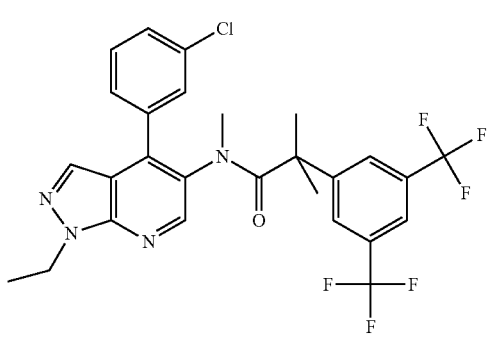 [SMILES: CCn1ncc2c(-c3cccc(Cl)c3)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 3-Chlorophenylboronic acid (commercially available)

ES-MS m/e: 569.2 (M+H$^+$).

Example 18

2-(3,5-Bis-trifluoromethyl-phenyl)-N-[4-(2,3-dichloro-phenyl)-1-ethyl-1H-pyrazolo[3,4-b]pyridin-5-yl]-N-methyl-isobutyramide

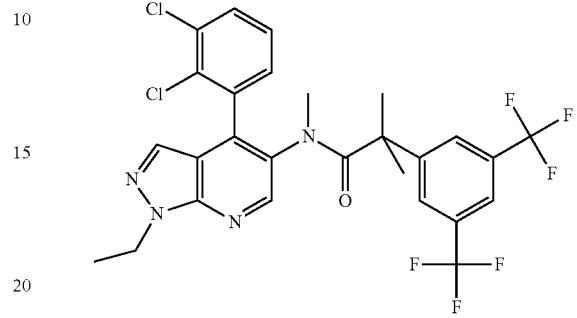

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2,3-Dichlorophenylboronic acid (commercially available) ES-MS m/e: 603.1 (M+H$^+$).

Example 19

2-(3,5-Bis-trifluoromethyl-phenyl)-N-[4-(2-chloro-4-fluoro-phenyl)-1-ethyl-1H-pyrazolo[3,4-b]pyridin-5-yl]-N-methyl-isobutyramide

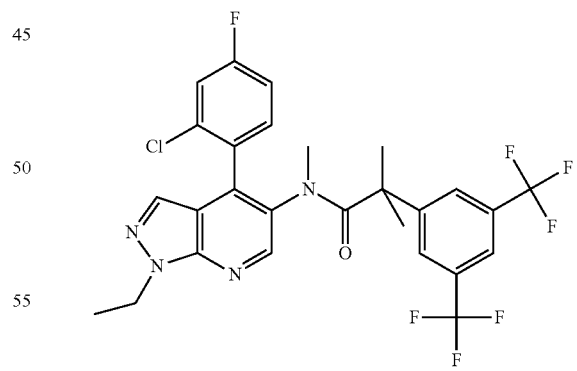

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2-Chloro-4-fluorophenylboronic acid (commercially available)

ES-MS m/e: 587.1 (M+H$^+$).

Example 20

2-(3,5-Bis-trifluoromethyl-phenyl)-N-[1-ethyl-4-(2-hydroxymethyl-phenyl)-1H-pyrazolo[3,4-b]pyridin-5-yl]-N-methyl-isobutyramide

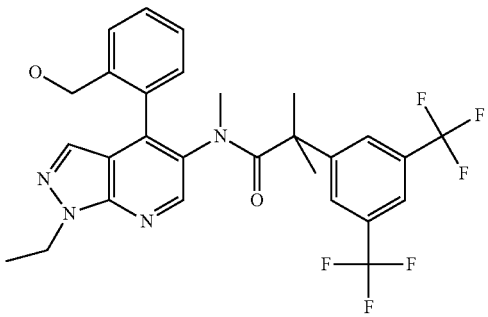 [SMILES: CCn1ncc2c(-c3ccccc3CO)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: (2-Hydroxymethylphenyl)boronic acid (commercially available)

ES-MS m/e: 565.2 (M+H$^+$).

Example 21

2-(3,5-Bis-trifluoromethyl-phenyl)-N-[1-ethyl-4-(4-methyl-thiophen-3-yl)-1H-pyrazolo[3,4-b]pyridin-5-yl]-N-methyl-isobutyramide

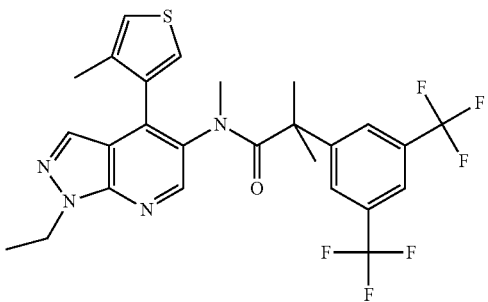 [SMILES: CCn1ncc2c(-c3cscc3C)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 4-Methyl-3-thiopheneboronic acid (commercially available)

ES-MS m/e: 555.2 (M+H$^+$)

Example 22

2-(3,5-Bis-trifluoromethyl-phenyl)-N-[4-(2-chloro-5-hydroxymethyl-phenyl)-1-ethyl-1H-pyrazolo[3,4-b]pyridin-5-yl]-N-methyl-isobutyramide

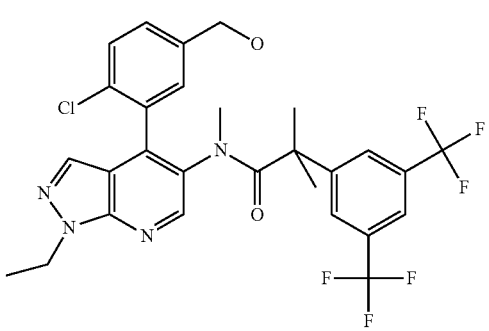 [SMILES: CCn1ncc2c(-c3cc(CO)ccc3Cl)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2-Chloro-5-hydroxymethylphenylboronic acid (commercially available)

ES-MS m/e: 599.1 (M+H$^+$).

Example 23

2-(3,5-Bis-trifluoromethyl-phenyl)-N-[4-(4-cyano-phenyl)-1-ethyl-1H-pyrazolo[3,4-b]pyridin-5-yl]-N-methyl-isobutyramide

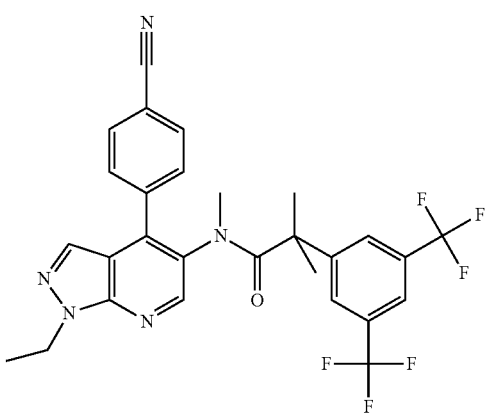 [SMILES: CCn1ncc2c(-c3ccc(C#N)cc3)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: (4-Cyanophenyl)boronic acid (commercially available)

ES-MS m/e: 560.2 (M+H$^+$).

Example 24

2-(3,5-Bis-trifluoromethyl-phenyl)-N-[4-(2-chloro-thiophen-3-yl)-1-ethyl-1H-pyrazolo[3,4-b]pyridin-5-yl]-N-methyl-isobutyramide

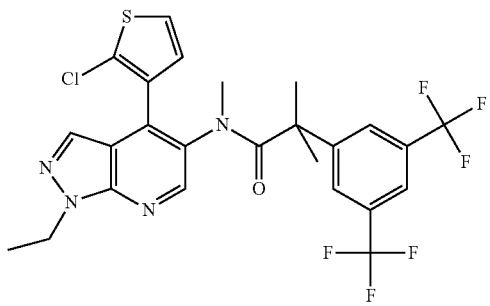 [SMILES: CCn1ncc2c(-c3ccsc3Cl)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2-Chlorothiophene-3-boronic acid (commercially available)

ES-MS m/e: 575.1 (M+H$^+$).

Example 25

2-(3,5-Bis-trifluoromethyl-phenyl)-N-[1-ethyl-4-(2-methyl-pyridin-3-yl)-1H-pyrazolo[3,4-b]pyridin-5-yl]-N-methyl-isobutyramide

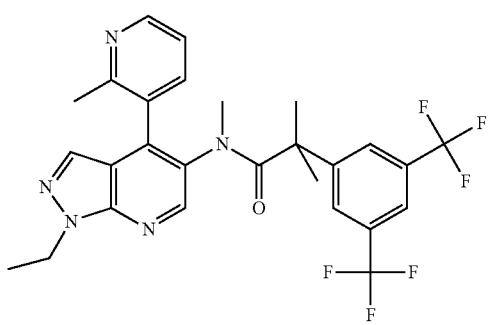 [SMILES: CCn1ncc2c(-c3cccnc3C)c(N(C)C(=O)C(C)(C)c3cc(C(F)(F)F)cc(C(F)(F)F)c3)cnc21]

Suzuki coupling according to general procedure I:

Pyrrazolo-pyridine intermediate: 2-(3,5-Bis-trifluoromethyl-phenyl)-N-(4-chloro-1-ethyl-1H-pyrazolo[3,4-b]pyridin-5-yl)-N-methyl-isobutyramide (XI-1)

Boronic acid: 2-Methylpyridine-3-boronic acid (commercially available)

ES-MS m/e: 550.3 (M+H$^+$).

Example 26

2-(3-fluoro-5-trifloromethyl-phenyl)-N-[1-ethyl-4-(4-fluoro-2-methyl-phenyl)-1H-pyrazolo[3,4-b]pyridin-5-yl]-N-methyl-isobutyramide

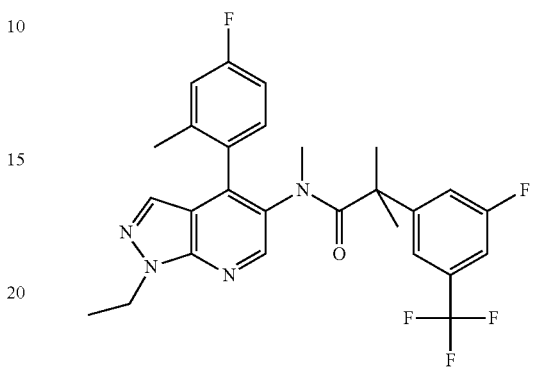

Amid coupling according to general procedure II:

Pyrrazolo-pyridine intermediate: [1-Ethyl-4-(4-fluoro-2-methyl-phenyl)-1H-pyrazolo[3,4-b]pyridin-5-yl]-methyl-amine (VII-1)

Acid chloride: 2-(3-Fluoro-5-trifluoromethyl-phenyl)-2-methyl-propionyl chloride (preparation described in WO2005002577) ES-MS m/e: 517.4 (M+H$^+$).

Example 27

2-(3,5-Dichloro-phenyl)-N-[1-ethyl-4-(4-fluoro-2-methyl-phenyl)-1H-pyrazolo[3,4-b]pyridin-5-yl]-N-methyl-isobutyramide

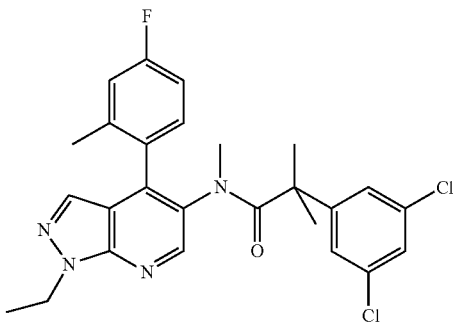 [SMILES: CCn1ncc2c(-c3ccc(F)cc3C)c(N(C)C(=O)C(C)(C)c3cc(Cl)cc(Cl)c3)cnc21]

Amid coupling according to general procedure II:

Pyrrazolo-pyridine intermediate: [1-Ethyl-4-(4-fluoro-2-methyl-phenyl)-1H-pyrazolo[3,4-b]pyridin-5-yl]-methyl-amine (VII-1)

Acid chloride: 2-(3,5-Dichloro-phenyl)-2-methyl-propionyl chloride (preparation described in WO2005002577) ES-MS m/e: 499.3 (M+H$^+$).

Example 28

2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide

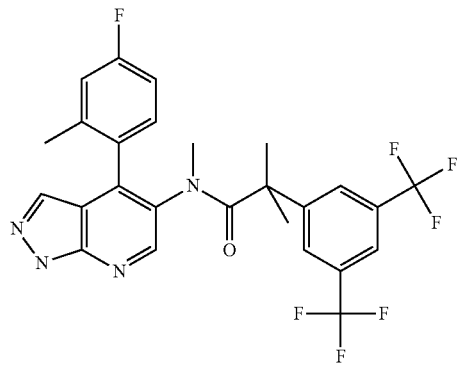

This compound was already described as the intermediate I-B-1 (see above). ES-MS m/e: 539.3 (M+H$^+$).

Example 29

2-(3-Chloro-phenyl)-N-[1-ethyl-4-(4-fluoro-2-methyl-phenyl)-1H-pyrazolo[3,4-b]pyridin-5-yl]-N-methyl-isobutyramide

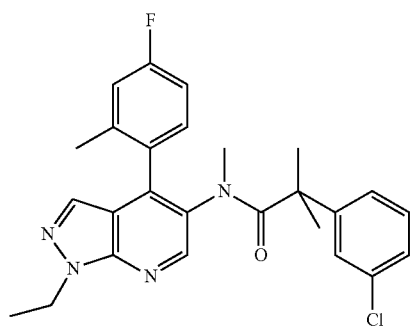 [SMILES: CCn1ncc2c(-c3ccc(F)cc3C)c(N(C)C(=O)C(C)(C)c3cccc(Cl)c3)cnc21]

Amid coupling according to general procedure II:
Pyrrazolo-pyridine intermediate: [1-Ethyl-4-(4-fluoro-2-methyl-phenyl)-1H-pyrazolo[3,4-b]pyridin-5-yl]-methyl-amine (VII-1)
Acid chloride: 2-(3-Chloro-phenyl)-2-methyl-propionyl chloride (preparation described in WO2005002577) ES-MS m/e: 465.1 (M+H$^+$).

Example 30

N-[1-Ethyl-4-(4-fluoro-2-methyl-phenyl)-1H-pyrazolo[3,4-b]pyridin-5-yl]-N-methyl-2-(3-trifluoromethyl-phenyl)-isobutyramide

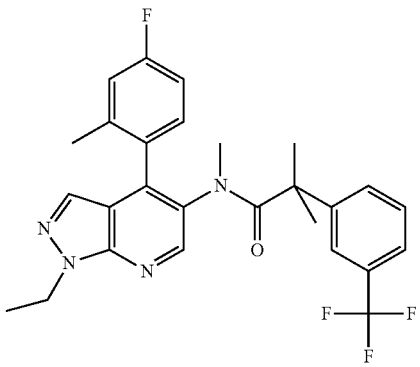 [SMILES: CCn1ncc2c(-c3ccc(F)cc3C)c(N(C)C(=O)C(C)(C)c3cccc(C(F)(F)F)c3)cnc21]

Amid coupling according to general procedure II:
Pyrrazolo-pyridine intermediate: [1-Ethyl-4-(4-fluoro-2-methyl-phenyl)-1H-pyrazolo[3,4-b]pyridin-5-yl]-methyl-amine (VII-1)
Acid chloride: 2-Methyl-2-(3-trifluoromethyl-phenyl)-propionyl chloride (preparation described in WO2005002577) ES-MS m/e: 499.3 (M+H$^+$).

Example 31

N-[1-Acetyl-4-(4-fluoro-2-methyl-phenyl)-1H-pyrazolo[3,4-b]pyridin-5-yl]-2-(3,5-bis-trifluoromethyl-phenyl)-N-methyl-isobutyramide

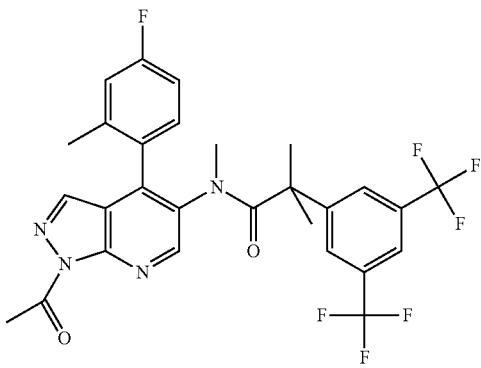 [SMILES: CC(=O)n1ncc2c(-c3ccc(F)cc3C)c(N(C)C(=O)C(C)(C)c3cc(C(F)(F)F)cc(C(F)(F)F)c3)cnc21]

Coupling according to general procedure III between:
Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and acetyl chloride (commercially available) ES-MS m/e: 581.2 (M+H$^+$).

Example 32

2-(3,5-Bis-trifluoromethyl-phenyl)-N-[4-(4-fluoro-2-methyl-phenyl)-1-(2-methoxy-acetyl)-1H-pyrazolo[3,4-b]pyridin-5-yl]-N-methyl-isobutyramide

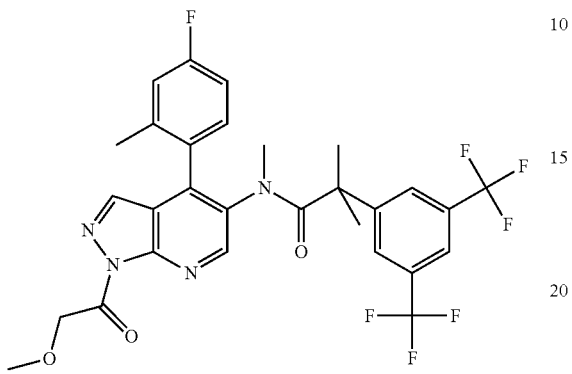

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and methoxy-acetyl chloride (commercially available) ES-MS m/e: 611.2 (M+H$^+$).

Example 33

2-(3,5-Bis-trifluoromethyl-phenyl)-N-[1-cyclopropanecarbonyl-4-(4-fluoro-2-methyl-phenyl)-1H-pyrazolo[3,4-b]pyridin-5-yl]-N-methyl-isobutyramide

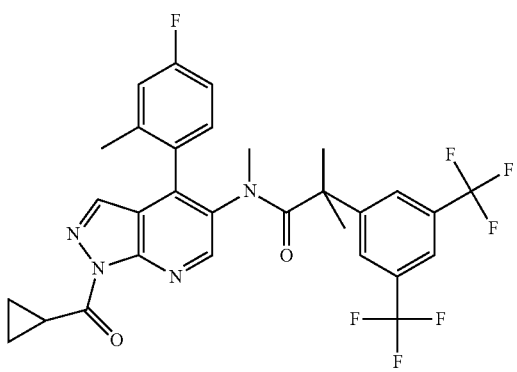 [SMILES: Cc1cc(F)ccc1-c1c(N(C)C(=O)C(C)(C)c2cc(C(F)(F)F)cc(C(F)(F)F)c2)cnc2c1cnn2C(=O)C1CC1]

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and cyclopropanecarbonyl chloride (commercially available) ES-MS m/e: 607.2 (M+H$^+$).

Example 34

2-(3,5-Bis-trifluoromethyl-phenyl)-N-[4-(4-fluoro-2-methyl-phenyl)-1-(2-oxo-2-pyrrolidin-1-yl-ethyl)-1H-pyrazolo[3,4-b]pyridin-5-yl]-N-methyl-isobutyramide

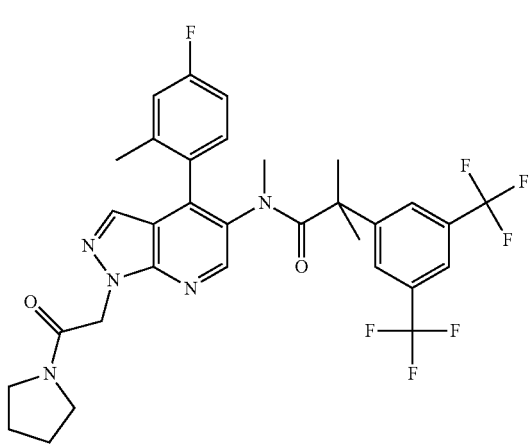 [SMILES: Cc1cc(F)ccc1-c1c(N(C)C(=O)C(C)(C)c2cc(C(F)(F)F)cc(C(F)(F)F)c2)cnc2c1cnn2CC(=O)N1CCCC1]

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and 2-bromo-1-(1-pyrrolidinyl)-1-ethanone (commercially available) ES-MS m/e: 650.4 (M+H$^+$).

Example 35

2-(3,5-Bis-trifluoromethyl-phenyl)-N-[1-dimethylcarbamoylmethyl-4-(4-fluoro-2-methyl-phenyl)-1H-pyrazolo[3,4-b]pyridin-5-yl]-N-methyl-isobutyramide

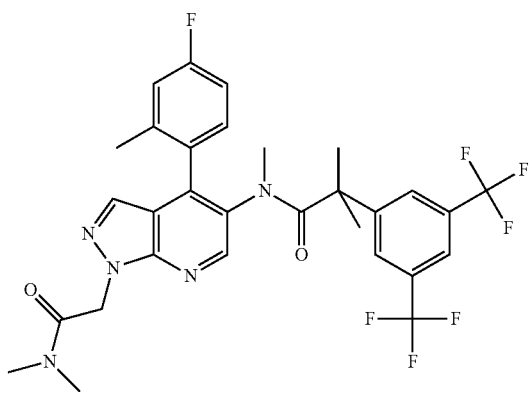 [SMILES: Cc1cc(F)ccc1-c1c(N(C)C(=O)C(C)(C)c2cc(C(F)(F)F)cc(C(F)(F)F)c2)cnc2c1cnn2CC(=O)N(C)C]

Coupling according to general procedure III between:

Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and 2-chloro-N,N-dimethylacetamide (commercially available) ES-MS m/e: 624.3 (M+H$^+$).

Example 36

2-(3,5-Bis-trifluoromethyl-phenyl)-N-[4-(4-fluoro-2-methyl-phenyl)-1-methanesulfonyl-1H-pyrazolo[3,4-b]pyridin-5-yl]-N-methyl-isobutyramide

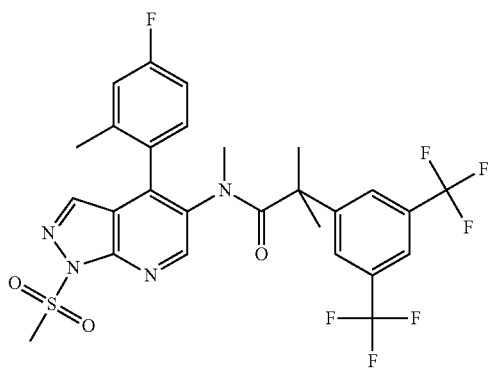 [SMILES: Cc1cc(F)ccc1-c1c(N(C)C(=O)C(C)(C)c2cc(C(F)(F)F)cc(C(F)(F)F)c2)cnc2c1cnn2S(C)(=O)=O]

Coupling according to general procedure III between:
Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and methanesulfonyl chloride (commercially available)
ES-MS m/e: 617.2 (M+H$^+$).

Example 37

2-(3,5-Bis-trifluoromethyl-phenyl)-N-[1-dimethylsulfamoyl-4-(4-fluoro-2-methyl-phenyl)-1H-pyrazolo[3,4-b]pyridin-5-yl]-N-methyl-isobutyramide

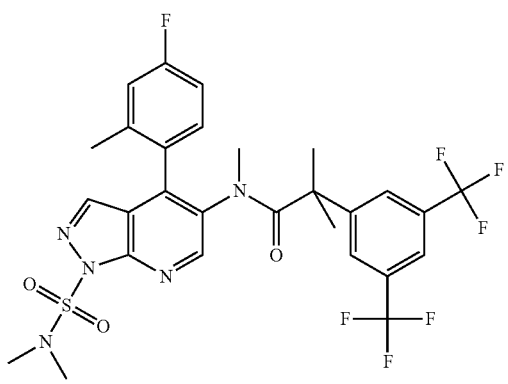 [SMILES: Cc1cc(F)ccc1-c1c(N(C)C(=O)C(C)(C)c2cc(C(F)(F)F)cc(C(F)(F)F)c2)cnc2c1cnn2S(=O)(=O)N(C)C]

Coupling according to general procedure III between:
Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and dimethylsulfamoyl chlorid (commercially available)
ES-MS m/e: 646.2 (M+H$^+$).

Example 38

2-(3,5-Bis-trifluoromethyl-phenyl)-N-[4-(4-fluoro-2-methyl-phenyl)-1-methanesulfonylmethyl-1H-pyrazolo[3,4-b]pyridin-5-yl]-N-methyl-isobutyramide

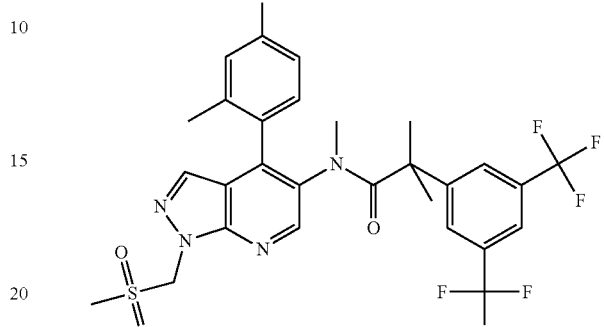

1$^{st}$ Step:
Preparation of the intermediate 2-(3,5-Bis-trifluoromethyl-phenyl)-N-[4-(4-fluoro-2-methyl-phenyl)-1-methylsulfanylmethyl-1H-pyrazolo[3,4-b]pyridin-5-yl]-N-methyl-isobutyramide:
Coupling according to general procedure III between:
Pyrrazolo-pyridine intermediate: 2-(3,5-Bis-trifluoromethyl-phenyl)-N-[4-(4-fluoro-2-methyl-phenyl)-1H-pyrazolo[3,4-b]pyridin-5-yl]-N-methyl-isobutyramide (I-B-1) and chloro-methylsulfanyl-methane (commercially available)
This compound was used directly in the next step.

2$^{nd}$ Step:
The above intermediate was dissolved in CH$_2$Cl$_2$ and mCPBA (2 eq.) was added. After one hour at RT, the reaction mixture was diluted in CH$_2$Cl$_2$, washed with an aqueous solution of NaHCO$_3$. The organic phase was dried over Na$_2$SO$_4$, concentrated under vacuo, purified by preparation HPLC to yield the title compound as a white solid (33%).
ES-MS m/e: 631.1 (M+H$^+$).

The invention claimed is:
1. A compound of formula I

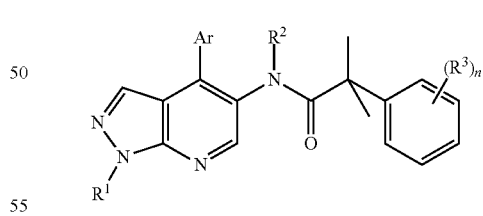

wherein
R$^1$ is hydrogen, lower alkyl, lower alkyl substituted by halogen, benzyl, —C(O)-lower alkyl, —C(O)—CH$_2$-lower alkoxy, —C(O)—C$_{3-6}$-cycloalkyl, —(CH$_2$)$_o$—C(O)—NRR', —(CH$_2$)$_o$S(O)$_2$-lower alkyl or —S(O)$_2$—NR,R';
o is 0 or 1;
R and R' are each independently hydrogen or lower alkyl, or together with the N atom to which they are attached form a 5 or 6 membered heterocycloalkyl ring;

R² is hydrogen or lower alkyl;

R³ is halogen, lower alkoxy, lower alkyl substituted by halogen or lower alkoxy substituted by halogen; and when n is 2, each R³ is the same or different;

n is 1 or 2;

Ar is phenyl optionally substituted by one or two substituents selected from lower alkyl, halogen, lower alkoxy, lower alkyl substituted by hydroxy or cyano, or is a five or six membered heteroaryl group, selected from thiophenyl or pyridinyl which are optionally substituted by lower alkyl or halogen;

or a pharmaceutically active acid-addition salt thereof.

2. The compound of claim 1, wherein Ar is optionally substituted phenyl and (R³)ₙ is 3,5-di-CF₃.

3. The compound of claim 2, selected from the group consisting of 2-(3,5-bis-trifluoromethyl-phenyl)-N-(1-ethyl-4-o-tolyl-1H-pyrazolo[3,4-b]pyridin-5-yl)-N-methyl-isobutyramide;

2-(3,5-bis-trifluoromethyl-phenyl)-N-[1-ethyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(2-chloro-phenyl)-1-ethyl-1H-pyrazolo[3,4-b]pyridin-5-yl]-N-methyl-isobutyramide;

2-(3,5-bis-trifluoromethyl-phenyl)-N-[4-(3,4-dichloro-phenyl)-1-ethyl-1H-pyrazolo[3,4-]pyridin-5-yl]-N-methyl-isobutyramide;

2-(3,5-bis-trifluoromethyl-phenyl)-N-[1-(2,2-difluoro-ethyl)-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methyl-1H-pyrazolo[3,4-b]pyridin-5-yl]-N-methyl-isobutyramide;

N-[1-benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;

2-(3,5-bis-trifluoromethyl-phenyl)-N-[1-ethyl-4-(4-fluoro-2-methoxy-phenyl)-1H-pyrazolo[3,4-b]pyridin-5-yl]-N-methyl-isobutyramide;

2-(3,5-bis-trifluoromethyl-phenyl)-N-[4-(2-chloro-3-fluoro-phenyl)-1-ethyl-1H-pyrazolo[3,4-b]pyridin-5-yl]-N-methyl-isobutyramide; and 2-(3,5-bis-trifluoromethyl-phenyl)-N-[4-(2,3-dichloro-phenyl)-1-ethyl-1H-pyrazolo[3,4-b]pyridin-5-yl]-N-methyl-isobutyramide.

4. The compound of claim 2, selected from the group consisting of 2-(3,5-bis-trifluoromethyl-phenyl)-N-[4-(2-chloro-4-fluoro-phenyl)-1-ethyl-1H-pyrazolo[3,4-b]pyridin-5-yl]-N-methyl-isobutyramide;

2-(3,5-bis-trifluoromethyl-phenyl)-N-[4-(2-chloro-5-hydroxymethyl-phenyl)-1-ethyl-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

N-[1-acetyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-(2-methoxy-acetyl)-1H-pyrazolo[3,4-b]pyridin-5-yl]-N-methyl-isobutyramide;

2-(3,5-bis-trifluoromethyl-phenyl)-N-[1-cyclopropanecarbonyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methanesulfonyl-1H-pyrazolo[3,4-b]pyridin-5-yl]-N-methyl-isobutyramide;

2-(3,5-bis-trifluoromethyl-phenyl)-N-[1-dimethylsulfamoyl-4-(4-fluoro-2-methyl-phenyl)-1H-pyrazolo[3,4-b]pyridin-5-yl]-N-methyl-isobutyramide; and 2-(3,5-bis-trifluoromethyl-phenyl)-N-[4-(4-fluoro-2-methyl-phenyl)-1-methanesulfonylmethyl-1H-pyrazolo[3,4-b]pyridin-5-yl]-N-methyl-isobutyramide.

5. The compound of claim 1, wherein Ar is an optionally substituted five or six membered heteroaryl group and (R³)ₙ is 3,5-di-CF₃.

6. The compound of claim 4, selected from the group consisting of 2-(3,5-bis-trifluoromethyl-phenyl)-N-[1-ethyl-4-(4-methyl-thiophen-3-yl)-1H-pyrazolo[3,4-b]pyridin-5-yl]-N-methyl-isobutyramide and 2-(3,5-bis-trifluoromethyl-phenyl)-N-[4-(2-chloro-thiophen-3-yl)-1-ethyl-1H-pyrazolo[3,4-b]pyridin-5-yl]-N-methyl-isobutyramide.

7. The compound of claim 1, wherein Ar is an optionally substituted phenyl and (R³)ₙ is halogen or lower alkyl.

8. The compound of claim 6, selected from the group consisting of 2-(3-fluoro-5-trifloromethyl-phenyl)-N-[1-ethyl-4-(4-fluoro-2-methyl-phenyl)-1H-pyrazolo[3,4-b]pyridin-5-yl]-N-methyl-isobutyramide and 2-(3,5-dichloro-phenyl)-N-[1-ethyl-4-(4-fluoro-2-methyl-phenyl)-1H-pyrazolo[3,4-b]pyridin-5-yl]-N-methyl-isobutyramide.

9. A pharmaceutical composition comprising a therapeutically effective amount of a compound of formula I

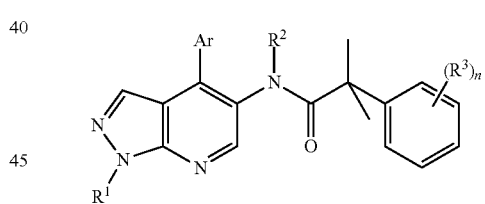

wherein

R¹ is hydrogen, lower alkyl, lower alkyl substituted by halogen, benzyl, —C(O)-lower alkyl, —C(O)—CH₂-lower alkoxy, —C(O)—C₃₋₆-cycloalkyl, —(CH₂)ₒ—C(O)—NRR', —(CH₂)ₒS(O)₂-lower alkyl or —S(O)₂—NR,R';

o is 0 or 1;

R and R' are each independently hydrogen or lower alkyl, or together with the N atom to which they are attached form a 5 or 6 membered heterocycloalkyl ring;

R² is hydrogen or lower alkyl;

R³ is halogen, lower alkoxy, lower alkyl substituted by halogen or lower alkoxy substituted by halogen; and when n is 2, each R³ is the same or different;

n is 1 or 2;

Ar is phenyl optionally substituted by one or two substituents selected from lower alkyl, halogen, lower alkoxy, lower alkyl substituted by hydroxy or cyano, or is a five or six membered heteroaryl group, selected from thiophenyl or pyridinyl which are optionally substituted by lower alkyl or halogen;
or a pharmaceutically active acid-addition salt thereof and a pharmaceutically acceptable salt thereof.

* * * * *